(12) United States Patent
Zhang et al.

(10) Patent No.: US 9,314,776 B2
(45) Date of Patent: Apr. 19, 2016

(54) COMPOSITE OXIDE, PREPARATION METHOD FOR SAME, AND APPLICATION THEREOF

(71) Applicants: CHINA PETROLEUM & CHEMICAL CORPORATION, Beijing (CN); FUSHUN RESEARCH INSTITUTE OF PETROLEUM AND PETROCHEMICALS, SINOPEC, Fushun, Liaoning (CN)

(72) Inventors: Shudong Zhang, Liaoning (CN); Yingjie Jin, Liaoning (CN); Xiangqian Ni, Liaoning (CN); Jie Li, Liaoning (CN); Xiwen Zhang, Liaoning (CN); Xinwei Zhang, Liaoning (CN)

(73) Assignees: CHINA PETROLEUM & CHEMICAL CORPORATION, Beijing (CN); FUSHUN RESEARCH INSTITUTE OF PETROLEUM AND PETROCHEMICALS, SINOPEC, Fushun, Liaoning (CN)

( * ) Notice: Subject to any disclaimer, the term of this patent is extended or adjusted under 35 U.S.C. 154(b) by 0 days.

(21) Appl. No.: 14/440,096

(22) PCT Filed: Oct. 10, 2013

(86) PCT No.: PCT/CN2013/001217
§ 371 (c)(1),
(2) Date: May 1, 2015

(87) PCT Pub. No.: WO2014/079142
PCT Pub. Date: May 30, 2014

(65) Prior Publication Data
US 2015/0321179 A1 Nov. 12, 2015

(30) Foreign Application Priority Data

Nov. 1, 2012 (CN) .......................... 2012 1 0427642
Nov. 1, 2012 (CN) .......................... 2012 1 0427646

(51) Int. Cl.
| | |
|---|---|
| *C07C 45/33* | (2006.01) |
| *B01J 23/00* | (2006.01) |
| *B01J 21/00* | (2006.01) |
| *B01J 37/00* | (2006.01) |
| *B01J 23/89* | (2006.01) |
| *B01J 23/652* | (2006.01) |
| *B01J 23/02* | (2006.01) |
| *B01J 21/04* | (2006.01) |
| *B01J 35/00* | (2006.01) |
| *B01J 35/02* | (2006.01) |
| *B01J 37/04* | (2006.01) |
| *B01J 37/16* | (2006.01) |
| *B01J 37/03* | (2006.01) |
| *B01J 37/08* | (2006.01) |
| *C07C 29/50* | (2006.01) |
| *B01J 23/46* | (2006.01) |
| *B01J 23/887* | (2006.01) |

(52) U.S. Cl.
CPC .............. *B01J 23/8993* (2013.01); *B01J 21/04* (2013.01); *B01J 23/00* (2013.01); *B01J 23/002* (2013.01); *B01J 23/02* (2013.01); *B01J 23/46* (2013.01); *B01J 23/6525* (2013.01); *B01J 23/887* (2013.01); *B01J 35/0006* (2013.01); *B01J 35/023* (2013.01); *B01J 37/035* (2013.01); *B01J 37/04* (2013.01); *B01J 37/08* (2013.01); *B01J 37/16* (2013.01); *C07C 29/50* (2013.01); *C07C 45/33* (2013.01); *B01J 23/89* (2013.01); *B01J 2523/00* (2013.01)

(58) Field of Classification Search
CPC .......... C07C 45/33; C07C 29/50; B01J 23/02; B01J 23/8993; B01J 21/04
USPC .................................. 568/482, 910; 502/312
See application file for complete search history.

(56) References Cited

U.S. PATENT DOCUMENTS

| | | | | |
|---|---|---|---|---|
| 4,918,238 A | * | 4/1990 | Costantini ............... | C07C 29/48 568/342 |
| 5,345,010 A | * | 9/1994 | Lyons ..................... | C07C 29/50 568/910 |

FOREIGN PATENT DOCUMENTS

| | | |
|---|---|---|
| CN | 101239316 A | 8/2008 |
| WO | 2010/133461 A1 | 11/2010 |

OTHER PUBLICATIONS

Ding, Shi et al. "Catalytic partial oxidation of methane over rhodium coated foam monolith" Journal of Chemical Industry and Engineering (China). vol. 58, No. 9, pp. 2255-2258 (Sep. 2007).
Qinghua Yang et al. "Development of C1 catalyst" Henan Chemical Industry. 1996, Issue 3, pp. 8-10.

* cited by examiner

*Primary Examiner* — Sikarl Witherspoon
(74) *Attorney, Agent, or Firm* — Novick, Kim & Lee, PLLC; Allen Xue

(57) ABSTRACT

This invention relates to a composite oxide, production and use thereof as a methane selective oxidizing catalyst. The composite oxide has a composition as illustrated by the formula $RhR_xMo_yV_zO_{\delta-\alpha}$, wherein the symbols are as defined in the specification. When used as a methane selective oxidizing catalyst, the present composite oxide provides a high methane conversion and a high selectivity to the aimed products.

17 Claims, 4 Drawing Sheets

COMPOSITE OXIDE, PREPARATION METHOD FOR SAME, AND APPLICATION THEREOF

TECHNICAL FIELD

Figure 1:
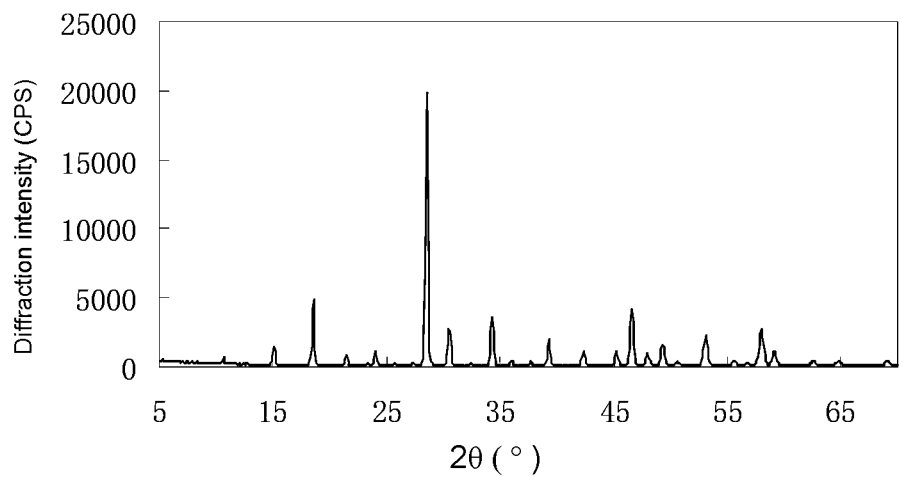

This invention relates to a composite oxide, specifically to a rhodium-vanadium-molybdenum based composite oxide. This invention further relates to a process for producing the composite oxide and use thereof as a methane selective oxidizing catalyst.

BACKGROUND ART

Selective oxidation of methane to produce aldehydes and alcohols opens new opportunities for the development and utilization of natural gas resource, and has been gained more and more attention. However, the prior art fails to develop a catalyst which gives an industrially acceptable aldehyde/alcohol yield up to now. The main reason lies in that methane is so inert that elevated temperatures should be involved for activation, at which temperature, not only the non-catalytic gas-phase oxidation reaction is enhance as a competition reaction, but also the selective oxidation product from the catalytic reaction is vulnerable to further oxidation due to its greater reaction activity than methane, and converted into a product with higher oxidation state, like CO, $CO_2$ and $H_2O$. For this reason, how to decrease the activation temperature of methane so as to enhance the selectivity to the aimed product remains one of the critical problems to be solved in this field. Further, the prior art mainly aims at developing a process for producing formaldehyde and methanol by a methane selective oxidation reaction, while few report concerns the technology for producing ethanol or acetaldehyde by a methane selective oxidation reaction.

Therefore, there is still a need for a methane selective oxidizing catalyst, which is especially suitable for co-producing ethanol and acetaldehyde by a methane selective oxidation reaction.

INVENTION SUMMARY

The present inventors, on the basis of the prior art, found a novel composite oxide, and further found that, the composite oxide is capable of acting as a catalyst for co-producing ethanol and acetaldehyde by a methane selective oxidation reaction, and then this invention is achieved.

Specifically, this invention relates to the following aspects.
1. A composite oxide, characterized by having a composition as represented by the formula $RhR_xMo_yV_zO_{\delta-\alpha}$, wherein R is Ni, Co or a combination of Ni and Co, x=0-3.0, preferably 0.01-3.0, more preferably 0.5-2.5, further preferably 1.0-2.0, y=0.1-0.9, preferably 0.2-0.7, more preferably 0.4-0.6, z=0.1-0.9, preferably 0.2-0.9, more preferably 0.5-0.8, δ is a positive number, representing a value with which the valency of oxygen in the composite oxide reaches a balance, α is α to δ/2, preferably 0 to δ/4, more preferably 0, when R represents the combination of Ni and Co, the ratio by molar of Ni:Co is 0.01-20:1, preferably 0.1-10:1, more preferably 1-3:1.
2. The composite oxide according to the preceding aspect, supported onto a carrier, wherein the ratio by weight of the composite oxide to the carrier is 0.01-1:1, preferably 0.1-0.5:1, more preferably 0.1-0.3:1, the carrier is one more inorganic refractory oxide, preferably one or more selected from the group consisting of $SiO_2$, $Al_2O_3$, $MgO$—$SiO_2$, $MgO$—$Al_2O_3$, $Al_2O_3$—$SiO_2$, $CaO$—$SiO_2$ and $CaO$—$MgO$—$SiO_2$, more preferably one or more selected from the group consisting of $SiO_2$, $Al_2O_3$, $MgO$—$SiO_2$ and $MgO$—$Al_2O_3$.
3. The composite oxide according to any one of the preceding aspects, preferably in a crystalline form, preferably in its powder X ray diffraction pattern, at least at the diffraction angle 2 theta of 28.5±0.5°, there is a diffraction peak, more preferably at least at each diffraction angle 2 theta of 18.5±0.5°, 28.5±0.5°, 31.5±0.5° and 34.5±0.5°, there is a diffraction peak.
4. A process for producing a composite oxide, characterized by including a step of optionally in the presence of a carrier, contacting (preferably by mixing) a Rh source, a Mo source, a V source and an optional Ni source and/or an optional Co source to conduct a reaction, so as to obtain the composite oxide, wherein the amount of the Rh source, the amount of the Mo source, the amount of the V source, the amount of the Ni source and the amount of the Co source are predetermined such that the obtained composite oxide has a composition as represented by the formula $RhR_xMo_yV_zO_{\delta-\alpha}$, wherein R is Ni, Co or a combination of Ni and Co, x=0-3.0, preferably 0.01-3.0, more preferably 0.5-2.5, further preferably 1.0-2.0, y=0.1-0.9, preferably 0.2-0.7, more preferably 0.4-0.6, z=0.1-0.9, preferably 0.2-0.9, more preferably 0.5-0.8, δ is a positive number, representing a value with which the valency of oxygen in the composite oxide reaches a balance, α is 0, when R represents the combination of Ni and Co, the ratio by molar of Ni:Co is 0.01-20:1, preferably 0.1-10:1, more preferably 1-3:1,
and optionally a step of partially reducing the composite oxide, so as to raise the α to a value in the range of from more than 0 to δ/2, preferably in the range of from more than 0 to δ/4.
5. The process according to any one of the preceding aspects, wherein the Rh source is one or more selected from the group consisting of oxides, hydroxides, inorganic acid salts and organic acid salts of Rh, preferably one or more selected from the group consisting of water soluble inorganic acid salts and water soluble organic acid salts of Rh, more preferably one or more selected from the group consisting of nitrates and acetates of Rh, the Ni source is one or more selected from the group consisting of oxides, hydroxides, inorganic acid salts and organic acid salts of Ni, preferably one or more selected from the group consisting of water soluble inorganic acid salts and water soluble organic acid salts of Ni, more preferably one or more selected from the group consisting of nitrates and acetates of Ni, the Co source is one or more selected from the group consisting of oxides, hydroxides, inorganic acid salts and organic acid salts of Co, preferably one or more selected from the group consisting of water soluble inorganic acid salts and water soluble organic acid salts of Co, more preferably one or more selected from the group consisting of nitrates and acetates of Co, the Mo source is one or more selected from the group consisting of oxides, hydroxides, inorganic acid salts, organic acid salts and ammonium oxometallates of Mo, preferably one or more selected from the group consisting of water soluble inorganic acid salts, water soluble organic acid salts and ammonium oxometallates of Mo, more preferably one or more selected from the group consisting of ammonium oxometallates of Mo, the V source is one or more selected from the group consisting of oxides, hydroxides, inorganic acid salts, organic acid salts and ammonium oxometallates of V, preferably one or more selected from the group consisting of water soluble inorganic acid salts, water soluble organic acid salts and ammonium oxometallates of V, more preferably one or more selected from the group consisting of ammonium oxometallates of V, the carrier is one or more selected from the group consisting of inorganic refractory oxides and precursors thereof, preferably one or more selected from the group consisting of $SiO_2$, $Al_2O_3$, $MgO-SiO_2$, $MgO-Al_2O_3$, $Al_2O_3-SiO_2$, $CaO-SiO_2$, $CaO-MgO-SiO_2$ and precursors thereof, more preferably one or more selected from the group consisting of $SiO_2$, $Al_2O_3$, $MgO-SiO_2$, $MgO-Al_2O_3$ and precursors thereof, and the amount of the carrier is predetermined such that the ratio by weight of the composite oxide to the carrier (calculated as the inorganic refractory oxide) is 0.01-1:1, preferably 0.1-0.5:1, more preferably 1-3:1.

6. The process according to any one of the preceding aspects, wherein the Rh source, the Mo source, the V source, the Ni source and the Co source are supplied in the form of aqueous solution, and these aqueous solutions are subject to a coprecipitation reaction to obtain an aqueous slurry, and after dehydrating, drying and calcinating the aqueous slurry, to obtain the composite oxide.

7. The process according to any one of the preceding aspects, wherein the reaction conditions include: a pH value of 3-10, preferably 5-9, under stirring, a reaction temperature of 60-90 degrees Celsius, preferably 70-80 degrees Celsius, a reaction duration of 1-12 h, preferably 3-10 h, the drying conditions include: a drying temperature of 60-150 degrees Celsius, preferably 100-120 degrees Celsius, a drying duration of 4-48 h, preferably 6-36 h, more preferably 8-24 h, the calcination conditions include: a calcination temperature of 400-900 degrees Celsius, preferably 500-700 degrees Celsius, more preferably 580-680 degrees Celsius, a calcination duration of 3-10 h, preferably 4-8 h.

8. The process according to any one of the preceding aspects, wherein the aqueous solution of the Mo source further contains ammonia at a concentration of 1-3 mol/L, and/or the aqueous solution of the V source further contains a $C_{2-6}$ polycarboxylic acid at a concentration of 0.1-0.5 mol/L, preferably oxalic acid.

9. Use of the composite oxide according to any one of the preceding aspects or a composite oxide produced in line with the process according to any one of the preceding aspects as a methane selective oxidizing catalyst.

10. A process for coproducing ethanol and acetaldehyde by a methane selective oxidation reaction, characterized by coproducing ethanol and acetaldehyde by a methane selective oxidation reaction in the presence of the composite oxide according to any one of the preceding aspects or a composite oxide produced in line with the process according to any one of the preceding aspects as the catalyst.

11. The process according to any one of the preceding aspects, wherein the reaction conditions for the methane selective oxidation reaction include: a reaction temperature of 300-800 degrees Celsius, preferably 400-700 degrees Celsius, more preferably 500-600 degrees Celsius, a reaction pressure of 0.1-5.0 MPa (gage), preferably 0.2-2.0 MPa (gage), more preferably 0.5-1.0 MPa (gage), a feeding gas composition (by molar) of $CH_4:O_2:H_2O=1:0.1-1:0.2-10$, preferably 1:0.25-0.5:2-4, a methane space velocity of 1200-3500 $h^{-1}$, preferably 2000-2800 $h^{-1}$.

TECHNICAL EFFECTS

As compared with the prior art, this invention has the following advantages. According to this invention, by an in-situ crystallization to produce the composite oxide, a catalyst suitable for coproducing ethanol and acetaldehyde by a methane selective oxidation reaction has been obtained for the first time in this field.

In the composite oxide according to this invention, the molybdenum-vanadium center responsible for methane selective oxidation and the rhodium center responsible for methanol carbonylation are bound together in a crystalline form, wherein the active phase of the crystalline form on the one hand supplies the d election hole, and on the other hand provides the lattice oxygen, whereby improving both the methane activation performance and the methane selective oxidation performance, resulting in improved methane conversion (for example, up to 17% or more) and improved selectivity to ethanol and acetaldehyde (i.e. a total selectivity of for example, up to 78% or more).

The composite oxide according to this invention is capable of catalyzing the methane selective oxidation at relatively reduced (for example, 1 MPa or less) reaction pressure.

The composite oxide according to this invention can be produced in a simple way, and therefore is suitable for production on an industrial scale.

FIGURE DESCRIPTION

FIG. 1 to FIG. 8 represent the powder X ray diffraction pattern of the composite oxide produced in each of Examples 1, 5, 9, 11, 12, 19, 25 and 28 respectively. The powder X ray diffraction pattern is obtained under conditions including: a Cu target, a Kα radiation source (λ=0.154056 nm), a tube voltage of 40 kV, a tube current of 80 mA, a scanning speed of 7.5° $min^{-1}$, a scanning step of 0.1°, a scanning range of 5-70°.

SPECIFIC MODE TO CARRY OUT THIS INVENTION

This invention will be described in details hereinafter with reference to the following specific embodiments. However, it should be noted that the protection scope of this invention should not be construed as limited to these specific embodiments, but rather determined by the attached claims.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern. Unless otherwise specified, percents, parts or ratios or the like mentioned in this specification are all on a weight basis.

According to this invention, related to is a composite oxide having a composition as represented by the formula $RhR_x Mo_y V_z O_{\delta-\alpha}$, wherein R is Ni, Co or a combination of Ni and Co, x=0-3.0, y=0.1-0.9, z=0.1-0.9, δ is a positive number, representing a value with which the valency of oxygen in the composite oxide reaches a balance, α=0-δ/2.

In the context of this specification, by "a value with which the valency of oxygen in the composite oxide reaches a balance", it refers to a value required by an electrically neutral composite oxide when Rh has a valency of +3, Mo has a valency of +6, V has a valency of +5, Ni has a valency of +2, Co has a valency of +2, O has a valency of −2 and α=0 in the composite oxide.

According to this invention, x=0-3.0, preferably 0.01-3.0, more preferably 0.5-2.5, further preferably 1.0-2.0.

According to this invention, y=0.1-0.9, preferably 0.2-0.7, more preferably 0.4-0.6. According to this invention, z=0.1-0.9, preferably 0.2-0.9, more preferably 0.5-0.8. According to this invention, α=0 to δ/2, preferably 0 to δ/4, more preferably 0. According to this invention, when R represents a combination of Ni and Co, by molar, Ni:Co=0.01-20:1, preferably 0.1-10:1, more preferably 1-3:1.

According to this invention, the composite oxide could be a supported composite oxide (for a simple description, also referred to as composite oxide herein), that is, the composite oxide being supported onto a carrier.

According to this invention, as the carrier, it is preferably an inorganic refractory oxide. As the inorganic refractory oxide, for example, there may be exemplified $SiO_2$, $Al_2O_3$, $MgO$—$SiO_2$, $MgO$—$Al_2O_3$, $Al_2O_3$—$SiO_2$, $CaO$—$SiO_2$ and $CaO$—$MgO$—$SiO_2$, preferably $SiO_2$, $Al_2O_3$, $MgO$—$SiO_2$, $MgO$—$Al_2O_3$ or a combination thereof.

According to this invention, there is no specific limitation as to the ratio of the composite oxide to the carrier, but by weight, is generally 0.01-1:1, preferably 0.1-0.5:1, more preferably 0.1-0.3:1.

According to this invention, the composite oxide preferably presents in a crystalline form. The crystalline form can be identified by a clear diffraction peak from the obtained powder X ray diffraction pattern in a powder X ray diffraction determination of the composite oxide (or the supported composite oxide).

According to this invention, when the composite oxide presents in a crystalline form, it is preferably that in its powder X ray diffraction pattern, at least at the diffraction angle 2 theta of 28.5±0.5° (for example, around 28.8), there is one strongest diffraction peak (also referred to as main diffraction peak), more preferably at least at each diffraction angle 2 theta of 18.5±0.5°, 28.5±0.5° (i.e. the main diffraction peak), 31.5±0.5° and 34.5±0.5°, there is a clear diffraction peak. For example, in the powder X ray diffraction pattern of the composite oxide produced in Example 9, at least at each diffraction angle 2 theta of 18.80°, 28.80°, 31.47° and 34.60°, there is a clear diffraction peak. These diffraction peaks correspond to the crystal planes [101], [103], [004] and [200] respectively, whose interplanar distance and relative diffraction intensity are characterized as follows.

| 2θ, ° | h, k, l | $d_{hkl}$, nm | $I/I_0$, % |
|---|---|---|---|
| 18.80 | 1, 0, 1 | 0.4761 | 20-40 |
| 28.80 | 1, 0, 3 | 0.3072 | 100 |
| 31.47 | 0, 0, 4 | 0.2843 | 10-30 |
| 34.60 | 2, 0, 0 | 0.2622 | 10-30 |

According to this invention, the composite oxide could be produced by the following process.

According to this invention, the process includes a step of contacting (successively or simultaneously) a Rh source, a Mo source, a V source and an optional Ni source and/or an optional Co source to conduct a reaction so as to obtain the composite oxide.

According to this invention, the amount of the Rh source, the amount of the Mo source, the amount of the V source, the amount of the Ni source (optional) and the amount of the Co source (optional) are predetermined such that the obtained composite oxide has a composition as represented by the formula $RhR_xMo_yV_zO_{\delta-\alpha}$ (α=0, referred to as composite oxide A hereinafter), wherein R is Ni, Co or a combination of Ni and Co, x=0-3.0, y=0.1-0.9, z=0.1-0.9, δ is a positive number, representing a value with which the valency of oxygen in the composite oxide reaches a balance (as hereinbefore defined).

According to this invention, x=0-3.0, preferably 0.01-3.0, more preferably 0.5-2.5, further preferably 1.0-2.0.

According to this invention, y=0.1-0.9, preferably 0.2-0.7, more preferably 0.4-0.6. According to this invention, z=0.1-0.9, preferably 0.2-0.9, more preferably 0.5-0.8. According to this invention, α=0 to δ/2, preferably 0 to δ/4, more preferably 0. According to this invention, when R is the combination of Ni and Co, by molar, Ni:Co=0.01-20:1, preferably 0.1-10:1, more preferably 1-3:1.

According to this invention, there is no specific limitation as to how to conduct the contacting, as long as the Rh source, the Mo source, the V source and the optional Ni source and/or the optional Co source are made to chemically react with one another so as to generate the composite oxide A, for example, there may be exemplified a method wherein these sources are (successively or simultaneously) mixed with one another in the form of solution or melt.

According to this invention, the contacting may be conducted in the presence of a carrier, whereby obtaining a supported composite oxide A (also referred to as composite oxide A).

According to this invention, as the carrier, it is preferably an inorganic refractory oxide or a precursor thereof. As the inorganic refractory oxide, for example, there may be exemplified $SiO_2$, $Al_2O_3$, $MgO$—$SiO_2$, $MgO$—$Al_2O_3$, $Al_2O_3$—$SiO_2$, $CaO$—$SiO_2$ and $CaO$—$MgO$—$SiO_2$, preferably $SiO_2$, $Al_2O_3$, $MgO$—$SiO_2$, $MgO$—$Al_2O_3$ or a combination thereof. By "precursor of the inorganic refractory oxide", it should be understood in a manner conventionally known in this field, and may refer to any material that can be converted into the inorganic refractory oxide during the process for producing the composite oxide of this invention (for example, by the calcination step as hereinafter described), for example, there may be exemplified aluminium nitrate, aluminium chloride, aluminium sulphate, aluminium isopropoxide, sodium silicate, ortho silicate ethyl ester, silica sol, magnesium nitrate, magnesium chloride, calcium nitrate, calcium chloride, preferably aluminium nitrate, aluminium chloride, aluminium sulphate, sodium silicate, ortho silicate ethyl ester, magnesium nitrate, calcium nitrate, more preferably aluminium nitrate, aluminium sulphate, sodium silicate, magnesium nitrate.

According to this invention, there is no specific limitation as to the amount of the carrier to be used herein, but is preferably predetermined such that the ratio by weight of the composite oxide A to the carrier (calculated as the inorganic refractory oxide) is 0.01-1:1, preferably 0.1-0.5:1, more preferably 0.1-0.3:1. According to this invention, as the Rh source, for example, there may be exemplified oxides, hydroxides, inorganic acid salts and organic acid salts (including hydrates thereof) of Rh, preferably water soluble inorganic acid salts and water soluble organic acid salts of Rh, more preferably nitrates and acetates of Rh, for example, $Rh(NO_3)_3$ or a hydrate thereof.

According to this invention, as the Ni source, for example, there may be exemplified oxides, hydroxides, inorganic acid salts and organic acid salts (including hydrates thereof) of Ni, preferably water soluble inorganic acid salts and water soluble organic acid salts of Ni, more preferably nitrates and acetates of Ni, for example, $Ni(NO_3)_2$ or a hydrate thereof.

According to this invention, as the Co source, for example, there may be exemplified oxides, hydroxides, inorganic acid salts and organic acid salts (including hydrates thereof) of Co, preferably water soluble inorganic acid salts and water soluble organic acid salts of Co, more preferably nitrates and acetates of Co, for example, $Co(NO_3)_2$ or a hydrate thereof.

According to this invention, as the Mo source, for example, there may be exemplified oxides, hydroxides, inorganic acid salts, organic acid salts and ammonium oxometallates (including hydrates thereof) of Mo, preferably water soluble inorganic acid salts, water soluble organic acid salts and ammonium oxometallates of Mo, more preferably ammonium oxometallates of Mo, for example, $(NH_4)_6Mo_7O_{24}$ or a hydrate thereof.

According to this invention, as the V source, for example, there may be exemplified oxides, hydroxides, inorganic acid salts, organic acid salts and ammonium oxometallates (including hydrates thereof) of V, preferably water soluble inorganic acid salts, water soluble organic acid salts and ammonium oxometallates of V, more preferably ammonium oxometallates of V, for example, $NH_4VO_3$ or a hydrate thereof.

According to a preferred embodiment of this invention, the Rh source, the Mo source, the V source, the Ni source (optional) and the Co source (optional) are provided in the form of aqueous solution, and optionally in the presence of the carrier, these aqueous solutions are (successively or simultaneously) mixed to conduct a reaction so as to obtain the composite oxide A.

According to a preferred embodiment of this invention, if provided in the form of aqueous solution, the aqueous solution of the Mo source may further contain 1-3 mol/L of ammonia.

According to a preferred embodiment of this invention, if provided in the form of aqueous solution, the aqueous solution of the V source may further contain 0.1-0.5 mol/L of a $C_{2-6}$ polycarboxylic acid (preferably a $C_{2-6}$ dicarboxylic acid, more preferably oxalic acid).

According to this invention, the reaction among the Rh source, the Mo source, the V source, the Ni source (optional) and the Co source (optional) is preferably conducted under stirring.

According to this invention, the reaction among the Rh source, the Mo source, the V source, the Ni source (optional) and the Co source (optional) is generally conducted under conditions: a pH value of 3-10 in the reaction system, preferably 5-9, a reaction temperature of 60-90 degrees Celsius, preferably 70-80 degrees Celsius, a reaction duration of 1-12 h, preferably 3-10 h.

After production, if needed, the composite oxide A according to this invention may be molded in a manner conventionally known in this field into a suitable particulate form, for example, bar, tablet, or cylinder.

In the process according to this invention, though not absolutely necessary, it is optional to further include a step of partially reducing the composite oxide A ($\alpha=0$), so as to make $\alpha$ to represent a value in the range of from more than 0 to $\delta/2$, preferably from more than 0 to $\delta/4$. This composite oxide is also referred to as composite oxide B.

According to this invention, there is no specific limitation as to how to conduct the partial reduction, as long as a part of the metal element(s) in the composite oxide A can be made to have a lowered valency (for example, $Ni^0$, $V^{3+}$ or $V^0$ and so on). This invention does not intend to specify which metal element will be subject to this partial reduction.

According to this invention, by the partial reduction, a composite oxide B will be obtained with a composition represented by the formula $RhR_xMo_yV_zO_{\delta-\alpha}$, wherein $\alpha$ is from more than 0 to $\delta/2$, preferably from more than 0 to $\delta/4$, and other symbols are as aforesaid defined.

According to this invention, as the partial reduction, for example, there may be exemplified a method of contacting the composite oxide A with a reducing agent (for example, hydrogen gas) under suitable reaction conditions to conduct a reduction reaction. As the reaction conditions, for example, there may be exemplified a reaction temperature of 60-600 degrees Celsius, a reaction pressure of 15-1500 psia, and a reaction duration sufficient for the composite oxide A to be partially reduced so as to raise the $\alpha$ to a value in the range of from more than 0 to $\delta/2$ (preferably from more than 0 to $\delta/4$), which is for example, 0.5-12 h, but not limiting thereto.

According to this invention, the composition of the composite oxide (including the composite oxide A and the composite oxide B) can be determined by ICP or XRF. According to a preferred embodiment of this invention, by the contacting, the Rh source, the Mo source, the V source and the optional Ni source and/or the optional Co source are made to conduct a coprecipitation reaction (or a neutralization reaction), whereby obtaining the composite oxide A in a crystalline form (referred to as in-situ crystallization).

According to the in-situ crystallization of this invention, the Rh source, the Mo source, the V source, the Ni source (optional) and the Co source (optional) are provided in the form of aqueous solution, and optionally in the presence of the carrier, these aqueous solutions are (successively or simultaneously) mixed to conduct the coprecipitation reaction, so as to obtain an aqueous slurry.

According to a preferred embodiment of this invention, if provided in the form of aqueous solution, the aqueous solution of the Mo source may further contain 1-3 mol/L of ammonia.

According to a preferred embodiment of this invention, if provided in the form of aqueous solution, the aqueous solution of the V source may further contain 0.1-0.5 mol/L of a $C_{2-6}$ polycarboxylic acid (preferably a $C_{2-6}$ dicarboxylic acid, more preferably oxalic acid).

For example, each of the Rh source, the Mo source, the V source, the Ni source (optional) and the Co source (optional) is dissolved in water and formulated into the corresponding aqueous solution respectively, and under stirring, these aqueous solutions and the optional carrier, at a predetermined amount respectively, are successively or simultaneously added (preferably firstly the carrier, and/or, finally the aqueous solution of the Mo source) to a reaction system (for example, a reactor), the reaction system is adjusted to a pH value of 3-10 (preferably 5-9, for example, with nitric acid or aqueous ammonia), at a reaction temperature of 60-90 degrees Celsius (preferably 70-80 degrees Celsius), the coprecipitation is conducted for 1-12 h (preferably 3-10 h), whereby obtaining the aqueous slurry.

Then, by dehydrating, optionally molding, drying and calcinating the aqueous slurry, the composite oxide A will be obtained.

According to this invention, the dehydration could be conducted in a manner conventionally known in this field, for example, there may be exemplified dehydration by evaporation or filtration.

According to this invention, the molding could be conducted in a manner conventionally known in this field (for example, extrusion, granulation), which is favorable for providing a suitable particulate form (for example, bar, tablet, or cylinder) for the composite oxide A.

According to this invention, the drying could be conducted in a manner conventionally known in this field, for example, there may be exemplified spray drying, vacuum drying, heating oven drying. If needed, the drying and the molding could be integrated into one single step. As the drying conditions, for example, there may be exemplified a drying temperature of 60-150 degrees Celsius, preferably 100-120 degrees Celsius, a drying duration of 4-48 h, preferably 6-36 h, more preferably 8-24 h.

According to this invention, by the calcination, the dried aqueous slurry may be totally converted into the composite oxide A in a crystalline form, and at the same time, the precursor of the inorganic refractory oxide (if any) will be converted into the corresponding inorganic refractory oxide. As the calcination conditions, for example, there may be exemplified a calcination temperature of 400-900 degrees Celsius, preferably 500-700 degrees Celsius, more preferably 580-680 degrees Celsius, a calcination duration of 3-10 h, preferably 4-8 h. If needed, the calcination could be conducted under an oxygen containing atmosphere (for example, air). According to this invention, further related to is use of the aforesaid composite oxide as a methane selective oxidizing catalyst. Specifically, this invention relates to a process for coproducing ethanol and acetaldehyde by a methane selective oxidation reaction, including a step of coproducing ethanol and acetaldehyde by a methane selective oxidation reaction in the presence of the aforesaid composite oxide as the catalyst.

According to this invention, the methane selective oxidation reaction conditions include: a reaction temperature of 300-800 degrees Celsius, preferably 400-700 degrees Celsius, more preferably 500-600 degrees Celsius, a reaction pressure of 0.1-5.0 MPa (gage), preferably 0.2-2.0 MPa (gage), more preferably 0.5-1.0 MPa (gage), by molar, a feeding gas composition of $CH_4:O_2:H_2O=1:0.1-1:0.2-10$, preferably 1:0.25-0.5:2-4, a methane space velocity of 1200-3500 $h^{-1}$, preferably 2000-2800 $h^{-1}$.

EXAMPLE

The present invention is further illustrated by using the following examples, but not limiting to same.

Example 1

2.4 g $Rh(NO_3)_3 \cdot 2H_2O$ was weighted and dissolved in 25 g deionized water, to obtain an aqueous solution of rhodium nitrate. 0.9 g $NH_4VO_3$ was dissolved in 25 g deionized water, then treated with oxalic acid at the same mole number as that of $NH_4VO_3$, to obtain a navy blue homogeneous solution containing a vanadium precursor, and mixed with the solution containing rhodium nitrate till homogeneous, heated in water bath to a temperature of 75 degrees Celsius. 0.6 g $(NH_4)_6Mo_7O_{24} \cdot 4H_2O$ was dissolved in 20.0 g of 8% (by weight) aqueous ammonia, to obtain an aqueous $(NH_4)_6Mo_7O_{24}$ ammonia solution. The solution was under stirring slowly dropwise added to the mixed solution containing rhodium nitrate and the vanadium precursor, adjusted with nitric acid or aqueous ammonia to a pH value of 5 or around, at 75 degrees Celsius stirred for 4 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhV_{0.9}Mo_{0.4}O_5$. 1.0 g of the composite oxide was used to conduct a methane selective oxidation reaction, with a feeding gas composition (by molar) of $CH_4:O_2:H_2O=2:1:4$, a methane space velocity of 2000 $h^{-1}$, the reaction was conducted at 1 MPa and 550 degrees Celsius for 4 h. Upon determination, the methane conversion is 6.5%, the total selectivity to ethanol and acetaldehyde is 63.7%.

The powder X ray diffraction pattern of the composite oxide produced in Example 1 was as illustrated in FIG. 1, indicating that the composite oxide presents in a crystalline form.

Example 2

2.4 g $Rh(NO_3)_3$ was weighted and dissolved in 25 g deionized water, to obtain an aqueous solution of rhodium nitrate. 0.9 g $NH_4VO_3$ was dissolved in 25 g deionized water, then treated with oxalic acid at the same mole number as that of $NH_4VO_3$, to obtain a navy blue homogeneous solution containing a vanadium precursor, and mixed with the solution containing rhodium nitrate till homogeneous, heated in water bath to a temperature of 75 degrees Celsius. 0.6 g $(NH_4)_6Mo_7O_{24} \cdot 4H_2O$ was dissolved in 20.0 g of 8% (by weight) aqueous ammonia, to obtain a $(NH_4)_6Mo_7O_{24}$ aqueous ammonia solution. The solution was under stirring slowly dropwise added to the mixed solution containing rhodium nitrate and the vanadium precursor, adjusted with nitric acid or aqueous ammonia to a pH value of 7 or around, at 75 degrees Celsius stirred for 4 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhV_{0.9}Mo_{0.4}O_5$. 1.0 g of the composite oxide was used to conduct a methane selective oxidation reaction, with a feeding gas composition (by molar) of $CH_4:O_2:H_2O=2:1:2$, a methane space velocity of 2000 $h^{-1}$, the reaction was conducted at 1.5 MPa and 500 degrees Celsius for 4 h. Upon determination, the methane conversion is 8.8%, the total selectivity to ethanol and acetaldehyde is 65.6%.

Example 3

2.4 g $Rh(NO_3)_3 \cdot 2H_2O$ was weighted and dissolved in 25 g deionized water, to obtain an aqueous solution of rhodium nitrate. 0.2 g $NH_4VO_3$ was dissolved in 25 g deionized water, then treated with oxalic acid at the same mole number as that of $NH_4VO_3$, to obtain a navy blue homogeneous solution containing a vanadium precursor, and mixed with the solution containing rhodium nitrate till homogeneous, heated in water bath to a temperature of 80 degrees Celsius. 0.3 g $(NH_4)_6Mo_7O_{24} \cdot 4H_2O$ was dissolved in 20.0 g of 8% (by weight) aqueous ammonia, to obtain a $(NH_4)_6Mo_7O_{24}$ aqueous ammonia solution. The solution was under stirring slowly dropwise added to the mixed solution containing rhodium nitrate and the vanadium precursor, adjusted with nitric acid or aqueous ammonia to a pH value of 5 or around, at 80 degrees Celsius stirred for 4 h, then the stirring was stopped, keeping the temperature constant at this value till no obvious water was generated, at 110 degrees Celsius dried for 16 h, at 500 degrees Celsius in air calcinated for 6 h, to obtain a composite oxide. The composite oxide has a composition of $RhV_{0.2}Mo_{0.2}O_{2.6}$. 1.0 g of the composite oxide was used to conduct a methane selective oxidation reaction, with a feeding gas composition (by molar) of $CH_4:O_2:H_2O=2:1:4$, a methane space velocity of 2000 $h^{-1}$, the reaction was conducted at 1 MPa and 550 degrees Celsius for 4 h. Upon determination, the methane conversion is 7.3%, the total selectivity to ethanol and acetaldehyde is 57.9%.

Example 4

6.0 g $Rh(NO_3)_3$ was weighted and dissolved in 25 g deionized water, to obtain an aqueous solution of rhodium nitrate. 1.8 g $NH_4VO_3$ was dissolved in 25 g deionized water, then treated with oxalic acid at the same mole number as that of $NH_4VO_3$, to obtain a navy blue homogeneous solution containing a vanadium precursor, and mixed with the solution containing rhodium nitrate till homogeneous, heated in water bath to a temperature of 70 degrees Celsius. 2.7 g $(NH_4)_6Mo_7O_{24}\cdot 4H_2O$ was dissolved in 20 g of 8% (by weight) aqueous ammonia, to obtain a $(NH_4)_6Mo_7O_{24}$ aqueous ammonia solution. The solution was under stirring slowly dropwise added to the mixed solution containing rhodium nitrate and the vanadium precursor, adjusted with nitric acid or aqueous ammonia to a pH value of 8 or around, at 70 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhV_{0.8}Mo_{0.8}O_{5.9}$. 1.0 g of the composite oxide was used to conduct a methane selective oxidation reaction, with a feeding gas composition (by molar) of $CH_4:O_2:H_2O=2:0.8:3$, a methane space velocity of 2400 $h^{-1}$, the reaction was conducted at 0.5 MPa and 550 degrees Celsius for 4 h. Upon determination, the methane conversion is 10.8%, the total selectivity to ethanol and acetaldehyde is 67.6%.

Example 5

7.9 g $Rh(NO_3)_3$ was weighted and dissolved in 25 g deionized water, to obtain an aqueous solution of rhodium nitrate. 1.8 g $NH_4VO_3$ was dissolved in 25 g deionized water, then treated with oxalic acid at the same mole number as that of $NH_4VO_3$, to obtain a navy blue homogeneous solution containing a vanadium precursor, and mixed with the solution containing rhodium nitrate till homogeneous, heated in water bath to a temperature of 75 degrees Celsius. 2.7 g $(NH_4)_6Mo_7O_{24}\cdot 4H_2O$ was dissolved in 20 g of 8% (by weight) aqueous ammonia, to obtain a $(NH_4)_6Mo_7O_{24}$ aqueous ammonia solution. The solution was under stirring slowly dropwise added to the mixed solution containing rhodium nitrate and the vanadium precursor, adjusted with nitric acid or aqueous ammonia to a pH value of 9 or around, at 75 degrees Celsius stirred for 6 h, then the stirring was stopped, keeping the temperature constant at this value till no obvious water was generated, at 100 degrees Celsius dried for 16 h, at 600 degrees Celsius in air calcinated for 8 h, to obtain a composite oxide. The composite oxide has a composition of $RhV_{0.7}Mo_{0.7}O_{5.4}$. 1.0 g of the composite oxide was used to conduct a methane selective oxidation reaction, with a feeding gas composition (by molar) of $CH_4:O_2:H_2O=2:0.6:4$, a methane space velocity of 2800 $h^{-1}$, the reaction was conducted at 2.0 MPa and 500 degrees Celsius for 4 h. Upon determination, the methane conversion is 12.9%, the total selectivity to ethanol and acetaldehyde is 74.8%.

Figure 2:
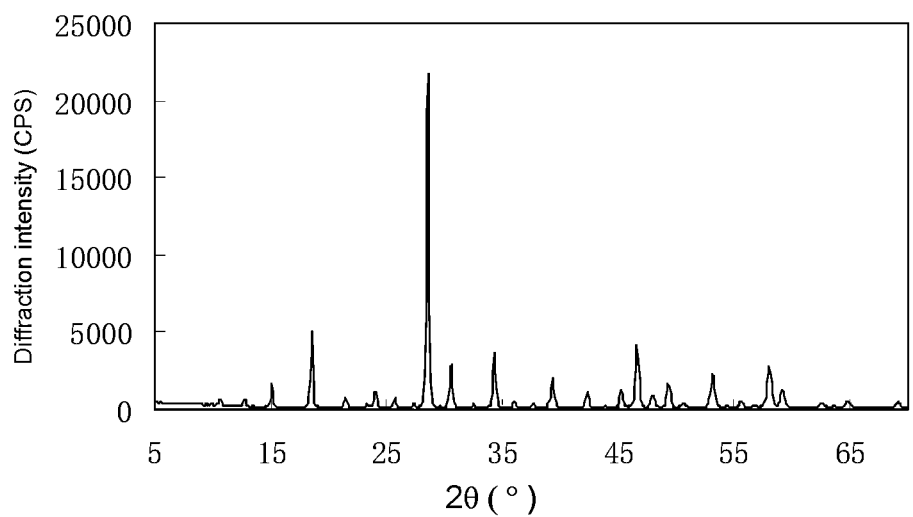

The powder X ray diffraction pattern of the composite oxide produced in Example 5 was as illustrated in FIG. 2, indicating that the composite oxide presents in a crystalline form.

Example 6

6.9 g $Rh(NO_3)_3$ was weighted and dissolved in 25 g deionized water, to obtain an aqueous solution of rhodium nitrate. 1.8 g $NH_4VO_3$ was dissolved in 25 g deionized water, then treated with oxalic acid at the same mole number as that of $NH_4VO_3$, to obtain a navy blue homogeneous solution containing a vanadium precursor, and mixed with the solution containing rhodium nitrate till homogeneous, heated in water bath to a temperature of 75 degrees Celsius. 2.7 g $(NH_4)_6Mo_7O_{24}\cdot 4H_2O$ was dissolved in 20 g of 8% (by weight) aqueous ammonia, to obtain a $(NH_4)_6Mo_7O_{24}$ aqueous ammonia solution. The solution was under stirring slowly dropwise added to the mixed solution containing rhodium nitrate and the vanadium precursor, adjusted with nitric acid or aqueous ammonia to a pH value of 7 or around, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhV_{0.7}Mo_{0.7}O_{5.4}$. 1.0 g of the composite oxide was used to conduct a methane selective oxidation reaction, with a feeding gas composition (by molar) of $CH_4:O_2:H_2O=2:0.8:4$, a methane space velocity of 2000 $h^{-1}$. The reaction was conducted at 1 MPa and 550 degrees Celsius for 4 h. Upon determination, the methane conversion is 12.4%, the total selectivity to ethanol and acetaldehyde is 76.3%.

Example 7

6.9 g $Rh(NO_3)_3$ was weighted and dissolved in 25 g deionized water, to obtain an aqueous solution of rhodium nitrate. 1.8 g $NH_4VO_3$ was dissolved in 25 g deionized water, then treated with oxalic acid at the same mole number as that of $NH_4VO_3$, to obtain a navy blue homogeneous solution containing a vanadium precursor, and mixed with the solution containing rhodium nitrate till homogeneous, there was added 7.0 g pseudo boehmite, heated in water bath to a temperature of 75 degrees Celsius. 2.7 g $(NH_4)_6Mo_7O_{24}\cdot 4H_2O$ was dissolved in 20 g of 8% (by weight) aqueous ammonia, to obtain a $(NH_4)_6Mo_7O_{24}$ aqueous ammonia solution. The solution was under stirring slowly dropwise added to the mixed solution containing rhodium nitrate and the vanadium precursor, adjusted with nitric acid or aqueous ammonia to a pH value of 7 or around, 75 degrees Celsius stirred for 6 h, then the stirring was stopped, keeping the temperature constant at this value till no obvious water was generated, at 110 degrees Celsius dried for 24 h, 600 degrees Celsius in air calcinated for 8 h, to obtain a composite oxide. The composite oxide has a composition of $RhV_{0.7}Mo_{0.7}O_{5.4}/Al_2O_3$. 1.0 g of the composite oxide was used to conduct a methane selective oxidation reaction, with a feeding gas composition (by molar) of $CH_4:O_2:H_2O=2:1:2$, a methane space velocity of 2000 $h^{-1}$. The reaction was conducted at 1 MPa and 550 degrees Celsius for 4 h. Upon determination, the methane conversion is 10.6%, the total selectivity to ethanol and acetaldehyde is 78.8%.

Example 8

6.9 g $Rh(NO_3)_3$ was weighted and dissolved in 25 g deionized water, to obtain an aqueous solution of rhodium nitrate. 1.8 g $NH_4VO_3$ was dissolved in 25 g deionized water, then treated with oxalic acid at the same mole number as that of $NH_4VO_3$, to obtain a navy blue homogeneous solution containing a vanadium precursor, and mixed with the solution containing rhodium nitrate till homogeneous, there was added 12.0 g pseudo boehmite containing 5% (by weight) of MgO, heated in water bath to a temperature of 75 degrees Celsius. 2.7 g $(NH_4)_6Mo_7O_{24}\cdot 4H_2O$ was dissolved in 20 g of 8% (by weight) aqueous ammonia, to obtain a $(NH_4)_6Mo_7O_{24}$ aqueous ammonia solution. The solution was under stirring slowly dropwise added to the mixed solution containing rhodium nitrate and the vanadium precursor, adjusted with nitric acid or aqueous ammonia to a pH value of 7 or around, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhV_{0.7}Mo_{0.7}O_{5.4}/MgO—Al_2O_3$. 1.0 g of the composite oxide was used to conduct a methane selective oxidation reaction, with a feeding gas composition (by molar) of $CH_4$:$O_2$:$H_2O$=2:1:4, a methane space velocity of 2000 $h^{-1}$. The reaction was conducted at 1 MPa and 600 degrees Celsius for 4 h. Upon determination, the methane conversion is 17.5%, the total selectivity to ethanol and acetaldehyde is 57.2%.

Example 9

6.9 g $Rh(NO_3)_3$ was weighted and dissolved in 25 g deionized water, to obtain an aqueous solution of rhodium nitrate. 1.8 g $NH_4VO_3$ was dissolved in 25 g deionized water, then treated with oxalic acid at the same mole number as that of $NH_4VO_3$, to obtain a navy blue homogeneous solution containing a vanadium precursor, and mixed with the solution containing rhodium nitrate till homogeneous, there was added 10.0 g silica having a MgO content of 5% by weight, heated in water bath to a temperature of 70 degrees Celsius. 2.7 g $(NH_4)_6Mo_7O_{24} \cdot 4H_2O$ was dissolved in 20 g of 8% (by weight) aqueous ammonia, to obtain a $(NH_4)_6Mo_7O_{24}$ aqueous ammonia solution. The solution was under stirring slowly dropwise added to the mixed solution containing rhodium nitrate and the vanadium precursor, adjusted with nitric acid or aqueous ammonia to a pH value of 6 or around, at 70 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhV_{0.7}Mo_{0.7}O_{5.4}/MgO—SiO_2$. 1.0 g of the composite oxide was used to conduct a methane selective oxidation reaction, with a feeding gas composition (by molar) of $CH_4$:$O_2$:$H_2O$=2:1:4, a methane space velocity of 2000 $h^{-1}$. The reaction was conducted at 1 MPa and 550 degrees Celsius for 4 h. Upon determination, the methane conversion is 13.8%, the total selectivity to ethanol and acetaldehyde is 73.7%.

Figure 3:
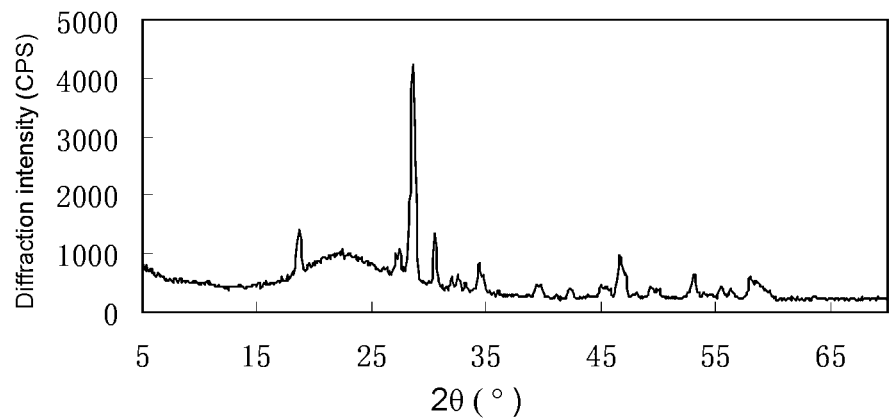

The powder X ray diffraction pattern of the composite oxide produced in Example 9 was as illustrated in FIG. 3, indicating that the composite oxide presents in a crystalline form.

Example 10

6.9 g $Rh(NO_3)_3$ was weighted and dissolved in 25 g deionized water, to obtain an aqueous solution of rhodium nitrate. 1.8 g $NH_4VO_3$ was dissolved in 25 g deionized water, then treated with oxalic acid at the same mole number as that of $NH_4VO_3$, to obtain a navy blue homogeneous solution containing a vanadium precursor, and mixed with the solution containing rhodium nitrate till homogeneous, heated in water bath to a temperature of 75 degrees Celsius. 2.7 g $(NH_4)_6Mo_7O_{24} \cdot 4H_2O$ was dissolved in 20 g of 8% (by weight) aqueous ammonia, to obtain a $(NH_4)_6Mo_7O_{24}$ aqueous ammonia solution. The solution was under stirring slowly dropwise added to the mixed solution containing rhodium nitrate and the vanadium precursor, adjusted with nitric acid or aqueous ammonia to a pH value of 7 or around, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhV_{0.6}Mo_{0.6}O_{5.8}$. The obtained composite oxide was reduced with hydrogen gas at a reduction pressure of 0.1 MPa, a reduction temperature of 350 degrees Celsius, a space velocity of 1000 $h^{-1}$, a reduction duration of 1 h. The thus reduced composite oxide has a composition of $RhV_{0.7}Mo_{0.7}O_{2.9}$. 1.0 g of the partially reduced composite oxide was used to conduct a methane selective oxidation reaction, with a feeding gas composition (by molar) of $CH_4$:$O_2$:$H_2O$=2:0.8:4, a methane space velocity of 2000 $h^{-1}$. The reaction was conducted at 1 MPa and 550 degrees Celsius for 4 h. Upon determination, the methane conversion is 7.3%, the total selectivity to ethanol and acetaldehyde is 61.2%.

Example 11

2.9 g $Co(NO_3)_2 \cdot 6H_2O$ and 4.9 g $Rh(NO_3)_3 \cdot 2H_2O$ were respectively weighted and dissolved in 35 g deionized water, to obtain a mixed solution containing cobalt nitrate and rhodium nitrate. 1.3 g $NH_4VO_3$ was dissolved in 20 g deionized water, then treated with oxalic acid at the same mole number as that of $NH_4VO_3$, to obtain a navy blue homogeneous solution containing a vanadium precursor, and mixed with the solution containing cobalt and rhodium till homogeneous, heated in water bath to a temperature of 75 degrees Celsius. 0.6 g $(NH_4)_6Mo_7O_{24} \cdot 4H_2O$ was dissolved in 20 g of 8% (by weight) aqueous ammonia, to obtain a $(NH_4)_6Mo_7O_{24}$ aqueous ammonia solution. The solution was under stirring slowly dropwise added to the mixed solution containing cobalt nitrate, rhodium nitrate and the vanadium precursor, adjusted with nitric acid or aqueous ammonia to a pH value of 5, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhCo_{0.5}V_{0.7}Mo_{0.2}O_{4.4}$. 1.0 g of the composite oxide was used to conduct a methane selective oxidation reaction, with a feeding gas composition (by molar) of $CH_4$:$O_2$:$H_2O$=2:1:4, a methane space velocity of 2000 $h^{-1}$, the reaction was conducted at 1 MPa and 550 degrees Celsius for 4 h. Upon determination, the methane conversion is 12.7%, the total selectivity to ethanol and acetaldehyde is 53.9%.

Figure 4:
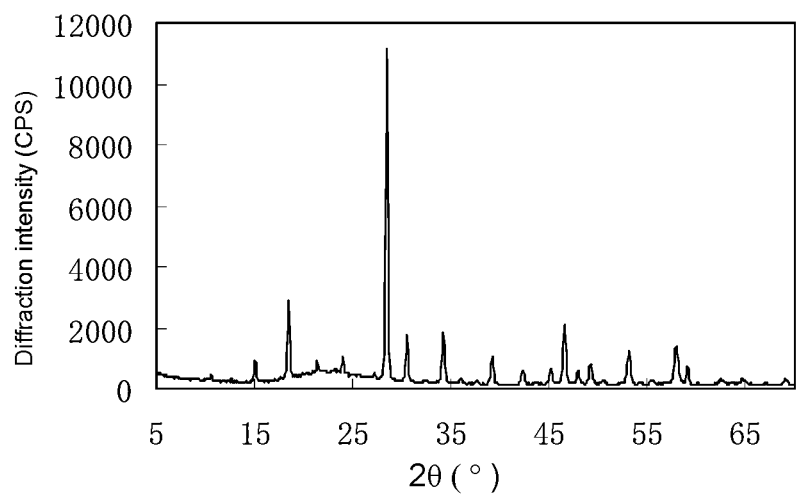

The powder X ray diffraction pattern of the composite oxide produced in Example 11 was as illustrated in FIG. 4, indicating that the composite oxide presents in a crystalline form.

Example 12

1.2 g $Ni(NO_3)_2 \cdot 6H_2O$ and 2.1 g $Rh(NO_3)_3 \cdot 2H_2O$ were respectively weighted and dissolved in 35 g deionized water, to obtain a mixed solution containing nickel nitrate and rhodium nitrate. 0.5 g $NH_4VO_3$ was added to 20 g deionized water, then treated with oxalic acid at the same mole number as that of $NH_4VO_3$, to obtain a navy blue homogeneous solution containing a vanadium precursor, and mixed with the acidic solution containing cobalt rhodium nitrates till homogeneous, heated in water bath to a temperature of 80 degrees Celsius. 1.0 g $(NH_4)_6Mo_7O_{24} \cdot 4H_2O$ was dissolved in 40 g of 8% (by weight) aqueous ammonia, to obtain a $(NH_4)_6Mo_7O_{24}$ aqueous ammonia solution. The solution was under stirring slowly dropwise added to the mixed solution containing nickel nitrate, rhodium nitrate and the vanadium precursor, adjusted with nitric acid or aqueous ammonia to a pH value of 10, at 80 degrees Celsius stirred for 4 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of RhNi$_{0.7}$V$_{0.7}$Mo$_{0.9}$O$_{6.7}$. 1.0 g of the composite oxide was used to conduct a methane selective oxidation reaction, with a feeding gas composition (by molar) of CH$_4$:O$_2$:H$_2$O=2:0.6:2, a methane space velocity of 2400 h$^{-1}$, the reaction was conducted at 1 MPa and 500 degrees Celsius for 4 h. Upon determination, the methane conversion is 8.9%, the total selectivity to ethanol and acetaldehyde is 57.6%.

Figure 5:
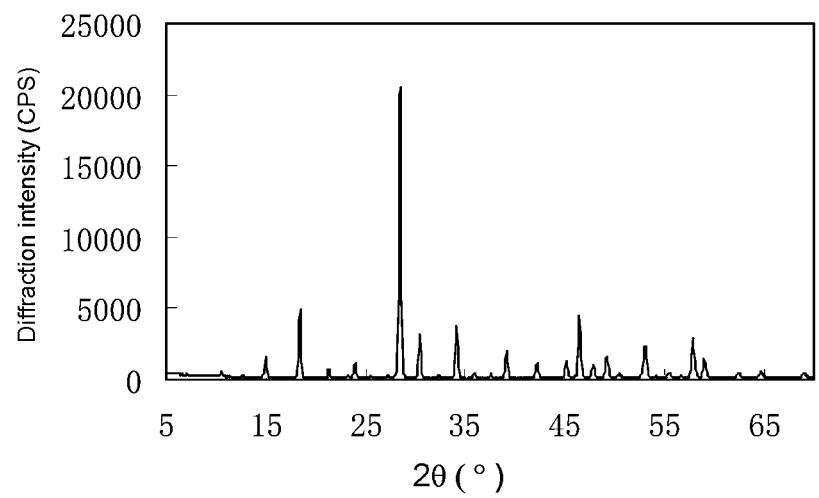

The powder X ray diffraction pattern of the composite oxide produced in Example 12 was as illustrated in FIG. 5, indicating that the composite oxide presents in a crystalline form.

Example 13

1.0 g Co(NO$_3$)$_2$.6H$_2$O, 1.9 g Ni(NO$_3$)$_2$.6H$_2$O and 2.1 g Rh(NO$_3$)$_3$.2H$_2$O were respectively weighted and dissolved in 35 g deionized water, to obtain a mixed solution containing cobalt nitrate, nickel nitrate and rhodium nitrate. 0.6 g NH$_4$VO$_3$ was added to 20 g deionized water, then treated with oxalic acid at the same mole number as that of NH$_4$VO$_3$, to obtain a navy blue homogeneous solution containing a vanadium precursor, and mixed with the acidic solution containing nickel, cobalt, rhodium nitrates till homogeneous, heated in water bath to a temperature of 70 degrees Celsius. 0.25 g (NH$_4$)$_6$Mo$_7$O$_{24}$.4H$_2$O was dissolved in 20 g of 8% (by weight) aqueous ammonia, to obtain a (NH$_4$)$_6$Mo$_7$O$_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 6, at 70 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of RhNi$_{1.0}$Co$_{0.5}$V$_{0.8}$Mo$_{0.2}$O$_{5.6}$. 1.0 g of the composite oxide was used to conduct a methane selective oxidation reaction, with a feeding gas composition (by molar) of CH$_4$:O$_2$:H$_2$O=2:0.8:2, a methane space velocity of 2400 h$^{-1}$, the reaction was conducted at 0.5 MPa and 500 degrees Celsius for 4 h. Upon determination, the methane conversion is 9.1%, the total selectivity to ethanol and acetaldehyde is 65.0%.

Example 14

2.2 g Co(NO$_3$)$_2$.6H$_2$O, 1.4 g Ni(NO$_3$)$_2$.6H$_2$O and 2.1 g Rh(NO$_3$)$_3$.2H$_2$O were respectively weighted and dissolved in 35 g deionized water, to obtain a mixed solution containing cobalt nitrate, nickel nitrate and rhodium nitrate. 0.5 g NH$_4$VO$_3$ was added to 20 g deionized water, then treated with oxalic acid at the same mole number as that of NH$_4$VO$_3$, to obtain a navy blue homogeneous solution containing a vanadium precursor, and mixed with the acidic solution containing nickel, cobalt, rhodium nitrates till homogeneous, heated in water bath to a temperature of 75 degrees Celsius. 0.6 g (NH$_4$)$_6$Mo$_7$O$_{24}$.4H$_2$O was dissolved in 20 g of 8% (by weight) aqueous ammonia, to obtain a (NH$_4$)$_6$Mo$_7$O$_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 7, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of RhNi$_{0.8}$Co$_{1.2}$V$_{0.7}$Mo$_{0.5}$O$_{6.8}$. 1.0 g of the composite oxide was used to conduct a methane selective oxidation reaction, with a feeding gas composition (by molar) of CH$_4$:O$_2$:H$_2$O=2:0.8:3, a methane space velocity of 2000 h$^{-1}$, the reaction was conducted at 2 MPa and 600 degrees Celsius for 4 h. Upon determination, the methane conversion is 14.7%, the total selectivity to ethanol and acetaldehyde is 67.7%.

Example 15

4.2 g Co(NO$_3$)$_2$.6H$_2$O, 4.3 g Ni(NO$_3$)$_2$.6H$_2$O and 9.8 g Rh(NO$_3$)$_3$.2H$_2$O were respectively weighted and dissolved in 35 g deionized water, to obtain a mixed solution containing cobalt nitrate, nickel nitrate and rhodium nitrate. 1.8 g NH$_4$VO$_3$ was added to 20 g deionized water, then treated with oxalic acid at the same mole number as that of NH$_4$VO$_3$, to obtain a navy blue homogeneous solution containing a vanadium precursor, and mixed with the acidic solution containing nickel, cobalt, rhodium nitrates till homogeneous, heated in water bath to a temperature of 75 degrees Celsius. 3.2 g (NH$_4$)$_6$Mo$_7$O$_{24}$.4H$_2$O was dissolved in 40 g of 8% (by weight) aqueous ammonia, to obtain a (NH$_4$)$_6$Mo$_7$O$_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 8, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of RhNi$_{0.5}$Co$_{0.5}$V$_{0.5}$Mo$_{0.6}$O$_{5.6}$. 1.0 g of the composite oxide was used to conduct a methane selective oxidation reaction, with a feeding gas composition (by molar) of CH$_4$:O$_2$:H$_2$O=2:1:2, a methane space velocity of 2800 h$^{-1}$, the reaction was conducted at 1 MPa and 550 degrees Celsius for 4 h. Upon determination, the methane conversion is 14.3%, the total selectivity to ethanol and acetaldehyde is 70.2%.

Example 16

2.8 g Co(NO$_3$)$_2$.6H$_2$O, 2.9 g Ni(NO$_3$)$_2$.6H$_2$O and 2.1 g Rh(NO$_3$)$_3$.2H$_2$O were respectively weighted and dissolved in 35 g deionized water, to obtain a mixed solution containing cobalt nitrate, nickel nitrate and rhodium nitrate. 0.7 g NH$_4$VO$_3$ was added to 20 g deionized water, then treated with oxalic acid at the same mole number as that of NH$_4$VO$_3$, to obtain a navy blue homogeneous solution containing a vanadium precursor, and mixed with the acidic solution containing nickel, cobalt, rhodium nitrates till homogeneous, heated in water bath to a temperature of 75 degrees Celsius. 1.0 g (NH$_4$)$_6$Mo$_7$O$_{24}$.4H$_2$O was dissolved in 40 g of 8% (by weight) aqueous ammonia, to obtain a (NH$_4$)$_6$Mo$_7$O$_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 8, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of RhNi$_{1.5}$Co$_{1.5}$V$_{0.9}$Mo$_{0.9}$O$_{10}$. 1.0 g of the composite oxide was used to conduct a methane selective oxidation reaction, with a feeding gas composition (by molar)

of $CH_4:O_2:H_2O=2:1:2$, a methane space velocity of $2800\,h^{-1}$, the reaction was conducted at 1 MPa and 550 degrees Celsius for 4 h. Upon determination, the methane conversion is 8.3%, the total selectivity to ethanol and acetaldehyde is 66.5%.

Example 17

0.4 g $Co(NO_3)_2.6H_2O$, 1.5 g $Ni(NO_3)_2.6H_2O$ and 2.1 g $Rh(NO_3)_3.2H_2O$ were respectively weighted and dissolved in 35 g deionized water, to obtain a mixed solution containing cobalt nitrate, nickel nitrate and rhodium nitrate. 0.25 g $NH_4VO_3$ was added to 20 g deionized water, then treated with oxalic acid at the same mole number as that of $NH_4VO_3$, to obtain a navy blue homogeneous solution containing a vanadium precursor, and mixed with the acidic solution containing nickel, cobalt, rhodium nitrates till homogeneous, heated in water bath to a temperature of 75 degrees Celsius. 0.9 g $(NH_4)_6Mo_7O_{24}.4H_2O$ was dissolved in 40 g of 8% (by weight) aqueous ammonia, to obtain a $(NH_4)_6Mo_7O_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 8, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhNi_{0.8}Co_{0.2}V_{0.3}Mo_{0.8}O_{4.2}$. 1.0 g of the composite oxide was used to conduct a methane selective oxidation reaction, with a feeding gas composition (by molar) of $CH_4:O_2:H_2O=2:1:2$, a methane space velocity of $2800\,h^{-1}$, the reaction was conducted at 1 MPa and 550 degrees Celsius for 4 h. Upon determination, the methane conversion is 12.7%, the total selectivity to ethanol and acetaldehyde is 68.5%.

Example 18

3.0 g $Co(NO_3)_2.6H_2O$, 0.7 g $Ni(NO_3)_2.6H_2O$ and 2.1 g $Rh(NO_3)_3.2H_2O$ were respectively weighted and dissolved in 35 g deionized water, to obtain a mixed solution containing cobalt nitrate, nickel nitrate and rhodium nitrate. 0.6 g $NH_4VO_3$ was added to 20 g deionized water, then treated with oxalic acid at the same mole number as that of $NH_4VO_3$, to obtain a navy blue homogeneous solution containing a vanadium precursor, and mixed with the acidic solution containing nickel, cobalt, rhodium nitrates till homogeneous, heated in water bath to a temperature of 75 degrees Celsius. 0.4 g $(NH_4)_6Mo_7O_{24}.4H_2O$ was dissolved in 40 g of 8% (by weight) aqueous ammonia, to obtain a $(NH_4)_6Mo_7O_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 8, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhNi_{0.4}Co_{1.6}V_{0.8}Mo_{0.3}O_{6.4}$. 1.0 g of the composite oxide was used to conduct a methane selective oxidation reaction, with a feeding gas composition (by molar) of $CH_4:O_2:H_2O=2:1:2$, a methane space velocity of $2800\,h^{-1}$, the reaction was conducted at 1 MPa and 550 degrees Celsius for 4 h. Upon determination, the methane conversion is 10.5%, the total selectivity to ethanol and acetaldehyde is 61.6%.

Example 19

Figure 6:
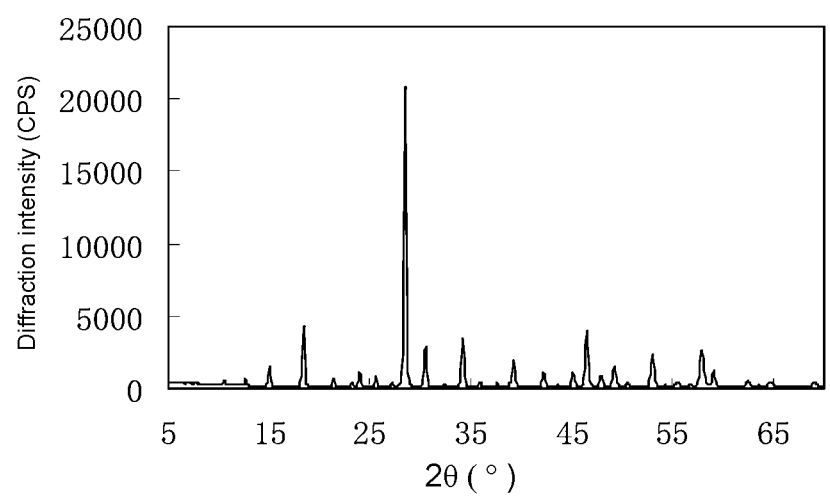

0.9 g $Co(NO_3)_2.6H_2O$, 0.9 g $Ni(NO_3)_2.6H_2O$ and 4.9 g $Rh(NO_3)_3.2H_2O$ were respectively weighted and dissolved in 35 g deionized water, to obtain a mixed solution containing cobalt nitrate, nickel nitrate and rhodium nitrate. 1.4 g $NH_4VO_3$ was added to 20 g deionized water, then treated with oxalic acid at the same mole number as that of $NH_4VO_3$, to obtain a navy blue homogeneous solution containing a vanadium precursor, and mixed with the acidic solution containing nickel, cobalt, rhodium nitrates till homogeneous, heated in water bath to a temperature of 75 degrees Celsius. 1.6 g $(NH_4)_6Mo_7O_{24}.4H_2O$ was dissolved in 30 g of 8% (by weight) aqueous ammonia, to obtain a $(NH_4)_6Mo_7O_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 7, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhNi_{0.2}Co_{0.2}V_{0.7}Mo_{0.6}O_{5.5}$. 1.0 g of the composite oxide was used to conduct a methane selective oxidation reaction, with a feeding gas composition (by molar) of $CH_4:O_2:H_2O=2:1:3$, a methane space velocity of $2000\,h^{-1}$, the reaction was conducted at 1.5 MPa and 550 degrees Celsius for 4 h. Upon determination, at 550 degrees Celsius, the methane conversion is 14.8% and the total selectivity to ethanol and acetaldehyde is 69.7%. The powder X ray diffraction pattern of the composite oxide produced in Example 19 was as illustrated in FIG. 6, indicating that the composite oxide presents in a crystalline form.

Example 20

1.0 g $Co(NO_3)_2.6H_2O$, 1.9 g $Ni(NO_3)_2.6H_2O$ and 2.1 g $Rh(NO_3)_3.2H_2O$ were respectively weighted and dissolved in 35 g deionized water, to obtain a mixed solution containing cobalt nitrate, nickel nitrate and rhodium nitrate. 0.4 g $NH_4VO_3$ was added to 20 g deionized water, then treated with oxalic acid at the same mole number as that of $NH_4VO_3$, to obtain a navy blue homogeneous solution containing a vanadium precursor, and mixed with the acidic solution containing nickel, cobalt, rhodium nitrates till homogeneous, heated in water bath to a temperature of 75 degrees Celsius. 0.8 g $(NH_4)_6Mo_7O_{24}.4H_2O$ was dissolved in 30 g of 8% (by weight) aqueous ammonia, to obtain a $(NH_4)_6Mo_7O_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 6, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhNi_{1.0}Co_{0.5}V_{0.5}Mo_{0.7}O_{6.4}$. 1.0 g of the composite oxide was used to conduct a methane selective oxidation reaction, with a feeding gas composition (by molar) of $CH_4:O_2:H_2O=2:1:4$, a methane space velocity of $2000\,h^{-1}$, the reaction was conducted at 2 MPa and 550 degrees Celsius for 4 h. Upon determination, the methane conversion is 15.1%, the total selectivity to ethanol and acetaldehyde is 73.2%.

Example 21

2.0 g $Co(NO_3)_2.6H_2O$, 3.8 g $Ni(NO_3)_2.6H_2O$ and 4.2 g $Rh(NO_3)_3.2H_2O$ were respectively weighted and dissolved in 35 g deionized water, to obtain a mixed solution containing cobalt nitrate, nickel nitrate and rhodium nitrate. 0.15 g $NH_4VO_3$ was added to 20 g deionized water, then treated with oxalic acid at the same mole number as that of $NH_4VO_3$, to obtain a navy blue homogeneous solution containing a vanadium precursor, and mixed with the acidic solution containing nickel, cobalt, rhodium nitrates till homogeneous, heated in water bath to a temperature of 75 degrees Celsius. 0.2 g $(NH_4)_6Mo_7O_{24}.4H_2O$ was dissolved in 30 g of 8% (by weight) aqueous ammonia, to obtain a $(NH_4)_6Mo_7O_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 6, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhNi_{1.0}Co_{0.5}V_{0.1}Mo_{0.1}O_{3.6}$. 1.0 g of the composite oxide was used to conduct a methane selective oxidation reaction, with a feeding gas composition (by molar) of $CH_4:O_2:H_2O=2:1:4$, a methane space velocity of 2000 $h^{-1}$, the reaction was conducted at 2 MPa and 550 degrees Celsius for 4 h. Upon determination, the methane conversion is 10.7%, the total selectivity to ethanol and acetaldehyde is 51.7%.

Example 22

1.0 g $Co(NO_3)_2.6H_2O$, 1.9 g $Ni(NO_3)_2.6H_2O$ and 2.1 g $Rh(NO_3)_3.2H_2O$ were respectively weighted and dissolved in 35 g deionized water, to obtain a mixed solution containing cobalt nitrate, nickel nitrate and rhodium nitrate. 0.4 g $NH_4VO_3$ was added to 20 g deionized water, then treated with oxalic acid at the same mole number as that of $NH_4VO_3$, to obtain a navy blue homogeneous solution containing a vanadium precursor, and mixed with the acidic solution containing nickel, cobalt, rhodium nitrates till homogeneous, heated in water bath to a temperature of 75 degrees Celsius. 0.8 g $(NH_4)_6Mo_7O_{24}.4H_2O$ was dissolved in 30 g of 8% (by weight) aqueous ammonia, to obtain a $(NH_4)_6Mo_7O_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 6, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a composite oxide. The composite oxide has a composition of $RhNi_{1.0}Co_{0.5}V_{0.5}Mo_{0.7}O_{6.4}$. The obtained composite oxide was reduced with hydrogen gas at a reduction pressure of 0.1 MPa, a reduction temperature of 350 degrees Celsius, a space velocity of 1000 $h^{-1}$, a reduction duration of 0.5 h. The thus reduced composite oxide has a composition of $RhNi_{1.0}Co_{0.5}V_{0.5}Mo_{0.7}O_{5.0}$. 1.0 g of the thus reduced composite oxide was used to conduct a methane selective oxidation reaction, with a feeding gas composition (by molar) of $CH_4:O_2:H_2O=2:1:4$, a methane space velocity of 2000 $h^{-1}$, the reaction was conducted at 2 MPa and 550 degrees Celsius for 4 h. Upon determination, the methane conversion is 13.7%, the total selectivity to ethanol and acetaldehyde is 63.6%.

Example 23

1.2 g $Co(NO_3)_2.6H_2O$, 1.2 g $Ni(NO_3)_2.6H_2O$ and 6.9 g $Rh(NO_3)_3.2H_2O$ were respectively weighted and dissolved in 35 g of a 20% (by weight) nitric acid solution, to obtain an acidic mixed solution containing nickel nitrate, cobalt nitrate and rhodium nitrate. 1.8 g $NH_4VO_3$ was added to 20 g deionized water, then treated with oxalic acid at the same mole number as that of $NH_4VO_3$, to obtain a navy blue homogeneous solution containing a vanadium precursor, and mixed with the acidic solution containing nickel, cobalt, rhodium nitrates till homogeneous, there was added 7.0 g pseudo boehmite, heated in water bath to a temperature of 75 degrees Celsius. 2.7 g $(NH_4)_6Mo_7O_{24}.4H_2O$ was dissolved in 30 g of 8% (by weight) aqueous ammonia, to obtain a $(NH_4)_6Mo_7O_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 7, at 75 degrees Celsius stirred for 6 h, under stirring evaporated till dry in water bath, at 110 degrees Celsius dried for 24 h, at 600 degrees Celsius in air calcinated for 8 h, to obtain a composite oxide. The composite oxide has a composition of $RhNi_{0.2}Co_{0.2}V_{0.7}Mo_{0.7}O_{5.8}/Al_2O_3$. 1.0 g of the composite oxide was used to conduct a methane selective oxidation reaction, with a feeding gas composition (by molar) of $CH_4:O_2:H_2O=2:1:2$, a methane space velocity of 2000 $h^{-1}$, the reaction was conducted at 1 MPa and 550 degrees Celsius for 4 h. Upon determination, the methane conversion is 15.6% and the total selectivity to ethanol and acetaldehyde is 69.4%.

Example 24

1.2 g $Co(NO_3)_2.6H_2O$, 1.2 g $Ni(NO_3)_2.6H_2O$ and 6.9 g $Rh(NO_3)_3.2H_2O$ were respectively weighted and dissolved in 35 g of a 20% (by weight) nitric acid solution, to obtain an acidic mixed solution containing nickel nitrate, cobalt nitrate and rhodium nitrate. 1.8 g $NH_4VO_3$ was added to 20 g deionized water, then treated with oxalic acid at the same mole number as that of $NH_4VO_3$, to obtain a navy blue homogeneous solution containing a vanadium precursor, and mixed with the acidic solution containing nickel, cobalt, rhodium nitrates till homogeneous, there was added 7.0 g pseudo boehmite, heated in water bath to a temperature of 75 degrees Celsius. 2.7 g $(NH_4)_6Mo_7O_{24}.4H_2O$ was dissolved in 30 g of 8% (by weight) aqueous ammonia, to obtain a $(NH_4)_6Mo_7O_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 7, at 75 degrees Celsius stirred for 6 h, under stirring evaporated till dry in water bath, at 110 degrees Celsius dried for 24 h, at 600 degrees Celsius in air calcinated for 8 h, to obtain a composite oxide. The composite oxide has a composition of $RhNi_{0.2}Co_{0.2}V_{0.75}Mo_{0.75}O_{6.4}/Al_2O_3$. The obtained composite oxide was reduced with hydrogen gas at a reduction pressure of 0.1 MPa, a reduction temperature of 350 degrees Celsius, a space velocity of 1000 $h^{-1}$, a reduction duration of 0.5 h. The thus reduced composite oxide has a composition of $RhNi_{0.2}Co_{0.2}V_{0.7}Mo_{0.7}O_{5.5}/

Al$_2$O$_3$. 1.0 g of the thus reduced composite oxide was used to conduct a methane selective oxidation reaction, with a feeding gas composition (by molar) of CH$_4$:O$_2$:H$_2$O=2:1:2, a methane space velocity of 2000 h$^{-1}$, the reaction was conducted at 1 MPa and 550 degrees Celsius for 4 h. Upon determination, the methane conversion is 15.1% and the total selectivity to ethanol and acetaldehyde is 68.9%.

Example 25

2.7 g Co(NO$_3$)$_2$.6H$_2$O, 2.7 g Ni(NO$_3$)$_2$.6H$_2$O and 3.0 g Rh(NO$_3$)$_3$.2H$_2$O were respectively weighted and dissolved in 35 g of a 20% (by weight) nitric acid solution, to obtain an acidic mixed solution containing nickel nitrate, cobalt nitrate and rhodium nitrate. 0.55 g NH$_4$VO$_3$ was added to 20 g deionized water, then treated with oxalic acid at the same mole number as that of NH$_4$VO$_3$, to obtain a navy blue homogeneous solution containing a vanadium precursor, and mixed with the acidic solution containing nickel, cobalt, rhodium nitrates till homogeneous, there was added 15.0 g silica having a MgO content of 5% by weight, heated in water bath to a temperature of 75 degrees Celsius. 1.0 g (NH$_4$)$_6$Mo$_7$O$_{24}$.4H$_2$O was dissolved in 30 g of 8% (by weight) aqueous ammonia, to obtain a (NH$_4$)$_6$Mo$_7$O$_{24}$ aqueous ammonia solution. The solution was under stirring slowly dropwise added to the mixed solution containing nickel nitrate, cobalt nitrate, rhodium nitrate and the vanadium precursor, adjusted with nitric acid or aqueous ammonia to a pH value of 7, at 75 degrees Celsius stirred for 6 h, under stirring evaporated till dry in water bath, 110 degrees Celsius dried for 24 h, at 600 degrees Celsius in air calcinated for 8 h, to obtain a composite oxide. The composite oxide has a composition of RhNi$_{1.0}$Co$_{1.0}$V$_{0.5}$Mo$_{0.6}$O$_{6.4}$/MgO—SiO$_2$. 1.0 g of the composite oxide was used to conduct a methane selective oxidation reaction, with a feeding gas composition (by molar) of CH$_4$:O$_2$:H$_2$O=2:1:4, a methane space velocity of 2400 h$^{-1}$, the reaction was conducted at 1 MPa and 550 degrees Celsius for 4 h. Upon determination, the methane conversion is 16.5% and the total selectivity to ethanol and acetaldehyde is 70.9%.

Figure 7:
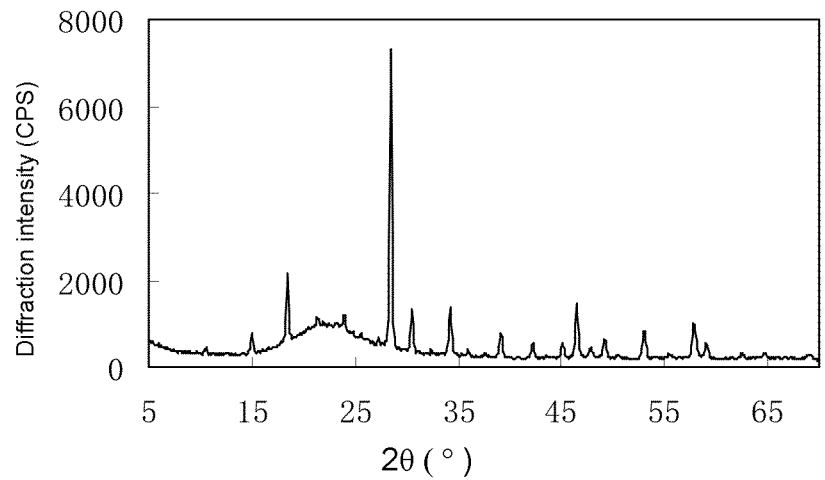

The powder X ray diffraction pattern of the composite oxide produced in Example 25 was as illustrated in FIG. 7, indicating that the composite oxide presents in a crystalline form.

Example 26

2.2 g Co(NO$_3$)$_2$.6H$_2$O, 1.4 g Ni(NO$_3$)$_2$.6H$_2$O and 2.1 g Rh(NO$_3$)$_3$.2H$_2$O were respectively weighted and dissolved in 35 g deionized water, to obtain a mixed solution containing cobalt nitrate, nickel nitrate and rhodium nitrate. 0.5 g NH$_4$VO$_3$ was added to 20 g deionized water, then treated with oxalic acid at the same mole number as that of NH$_4$VO$_3$, to obtain a navy blue homogeneous solution containing a vanadium precursor, and mixed with the acidic solution containing nickel, cobalt, rhodium nitrates till homogeneous, heated in water bath to a temperature of 75 degrees Celsius. An 8% (by weight) aqueous ammonia solution was under stirring slowly dropwise added to the mixed solution containing nickel nitrate, cobalt nitrate, rhodium nitrate and the vanadium precursor, adjusted with nitric acid or aqueous ammonia to a pH value of 7, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a Co—Ni—Rh—V based composite oxide. 0.6 g (NH$_4$)$_6$Mo$_7$O$_{24}$.4H$_2$O was dissolved in 20 g deionized water, to obtain an aqueous solution of (NH$_4$)$_6$Mo$_7$O$_{24}$. The aqueous solution containing Mo was added to the Co—Ni—Rh—V based composite oxide, at room temperature aged for 2 h, at 110 degrees Celsius dried for 24 h, at 600 degrees Celsius in air calcinated for 8 h, to obtain a composite oxide having the same composition as that of Example 14. The composite oxide has a composition of RhNi$_{0.8}$Co$_{1.2}$V$_{0.7}$Mo$_{0.5}$O$_{6.8}$. 1.0 g of the composite oxide was used to conduct a methane selective oxidation reaction, with a feeding gas composition (by molar) of CH$_4$:O$_2$:H$_2$O=2:0.8:3, a methane space velocity of 2000 h$^{-1}$, the reaction was conducted at 2 MPa and 600 degrees Celsius for 4 h. Upon determination, the methane conversion is 3.7%, the total selectivity to ethanol and acetaldehyde is 5.7%.

Example 27

2.2 g Co(NO$_3$)$_2$.6H$_2$O, 1.4 g Ni(NO$_3$)$_2$.6H$_2$O and 2.1 g Rh(NO$_3$)$_3$.2H$_2$O were respectively weighted and dissolved in 35 g deionized water, to obtain a mixed solution containing cobalt nitrate, nickel nitrate and rhodium nitrate. 0.5 g NH$_4$VO$_3$ was added to 20 g deionized water, then treated with oxalic acid at the same mole number as that of NH$_4$VO$_3$, to obtain a navy blue homogeneous solution containing a vanadium precursor, and mixed with the acidic solution containing nickel, cobalt, rhodium nitrates till homogeneous, heated in water bath to a temperature of 75 degrees Celsius. An 8% (by weight) aqueous ammonia solution was under stirring slowly dropwise added to the mixed solution containing nickel nitrate, cobalt nitrate, rhodium nitrate and the vanadium precursor, adjusted with nitric acid or aqueous ammonia to a pH value of 7, at 75 degrees Celsius stirred for 6 h, then the stirring was stopped, keeping the temperature constant at this value till no obvious water was generated, at 110 degrees Celsius dried for 24 h, at 600 degrees Celsius in air calcinated for 8 h, to obtain a Co—Ni—Rh—V based composite oxide. 0.6 g (NH$_4$)$_6$Mo$_7$O$_{24}$.4H$_2$O was dissolved in 20 g deionized water, to obtain an aqueous solution of (NH$_4$)$_6$Mo$_7$O$_{24}$. The aqueous solution containing Mo was added to the Co—Ni—Rh—V based composite oxide, at room temperature aged for 2 h, at 110 degrees Celsius dried for 24 h, at 600 degrees Celsius in air calcinated for 8 h, to obtain a composite oxide having the same composition as that of Example 14. The composite oxide has a composition of RhNi$_{0.8}$Co$_{1.2}$V$_{0.7}$Mo$_{0.5}$O$_{6.8}$. The obtained composite oxide was reduced with hydrogen gas at a reduction pressure of 0.1 MPa, a reduction temperature of 350 degrees Celsius, a space velocity of 1000 h$^{-1}$, a reduction duration of 0.5 h. The thus reduced composite oxide has a composition of RhNi$_{0.8}$Co$_{1.2}$V$_{0.7}$Mo$_{0.5}$O$_{3.7}$. 1.0 g of the composite oxide was used to conduct a methane selective oxidation reaction, with a feeding gas composition (by molar) of CH$_4$:O$_2$:H$_2$O=2:0.8:3, a methane space velocity of 2000 h$^{-1}$, the reaction was conducted at 2 MPa and 600 degrees Celsius for 4 h. Upon determination, the methane conversion is 5.5%, the total selectivity to ethanol and acetaldehyde is 0.7%.

Example 28

An impregnation method was used to produce a γ-alumina supported rhodium-vanadium-molybdenum based composite oxide. 6.9 g Rh(NO$_3$)$_3$.2H$_2$O was weighted and dissolved in 10 g deionized water, to obtain an aqueous solution of rhodium nitrate. 1.8 g NH$_4$VO$_3$ was dissolved in 10 g deionized water, then treated with oxalic acid at the same mole number as that of NH$_4$VO$_3$, to obtain a navy blue homogeneous solution containing a vanadium precursor. 2.7 g (NH$_4$)$_6$Mo$_7$O$_{24}$.4H$_2$O was dissolved in 10 g deionized water, to obtain an aqueous solution of $(NH_4)_6Mo_7O_{24}$. The three solutions were successively supported by impregnation onto γ-alumina made of 7.0 g pseudo boehmite in different steps, with each impregnation step followed by drying at 110 degrees Celsius for 24 h and calcination in air at 600 degrees Celsius for 8 h, to obtain a composite oxide having the same composition as that of Example 7. The composite oxide has a composition of $RhV_{0.7}Mo_{0.7}O_{5.4}/Al_2O_3$. 1.0 g of the composite oxide was used to conduct a methane selective oxidation reaction, with a feeding gas composition (by molar) of $CH_4:O_2:H_2O=2:1:2$, a methane space velocity of 2000 $h^{-1}$. The reaction was conducted at 1 MPa and 550 degrees Celsius for 4 h. Upon determination, the methane conversion is 8.6%, the total selectivity to ethanol and acetaldehyde is 0.5%.

Figure 8:
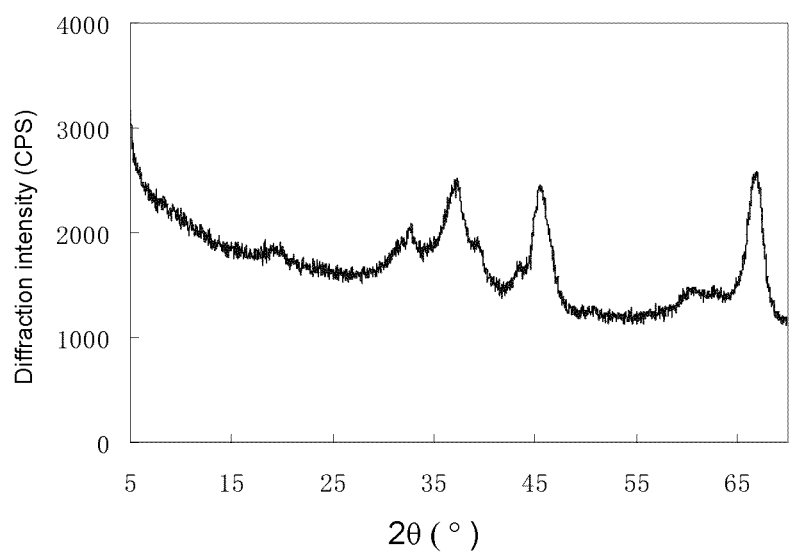

The powder X ray diffraction pattern of the composite oxide produced in Example 28 was as illustrated in FIG. 8, indicating that the composite oxide is not in a crystalline form.

Example 29

An impregnation method was used to produce a γ-alumina supported rhodium-vanadium-molybdenum based composite oxide. 1.2 g $Co(NO_3)_2 \cdot 6H_2O$, 1.2 g $Ni(NO_3)_2 \cdot 6H_2O$ and 6.9 g $Rh(NO_3)_3 \cdot 2H_2O$ were weighted and dissolved in 10 g deionized water, to obtain an aqueous solution of cobalt nitrate, nickel nitrate, rhodium nitrate. 1.8 g $NH_4VO_3$ was dissolved in 10 g deionized water, then treated with oxalic acid at the same mole number as that of $NH_4VO_3$, to obtain a navy blue homogeneous solution containing a vanadium precursor. 2.7 g $(NH_4)_6Mo_7O_{24} \cdot 4H_2O$ was dissolved in 10 g deionized water, to obtain an aqueous solution of $(NH_4)_6Mo_7O_{24}$. The three solutions were successively supported by impregnation onto γ-alumina made of 7.0 g pseudo boehmite in different steps, with each impregnation step followed by drying at 110 degrees Celsius for 24 h and calcination in air at 600 degrees Celsius for 8 h, to obtain a composite oxide having the same composition as that of Example 23. The composite oxide has a composition of $RhNi_{0.2}Co_{0.2}V_{0.7}Mo_{0.7}O_{5.8}/Al_2O_3$. 1.0 g of the composite oxide was used to conduct a methane selective oxidation reaction, with a feeding gas composition (by molar) of $CH_4:O_2:H_2O=2:1:2$, a methane space velocity of 2000 $h^{-1}$. The reaction was conducted at 1 MPa and 550 degrees Celsius for 4 h. Upon determination, the methane conversion is 10.9%, the total selectivity to ethanol and acetaldehyde is 0.3%.

We claim:

1. A composite oxide, comprising a composition represented by a formula $RhR_xMo_yV_zO_{\delta-\alpha}$,
    wherein R is Ni, Co or a combination of Ni and Co, x=0-3.0, y=0.1-0.9, z=0.1-0.9, δ is a positive number at which a valency of oxygen in the composite oxide reaches a balance, α is 0 to δ/2,
    wherein when R represents the combination of Ni and Co, a molar ratio of Ni:Co is 0.01-20:1.

2. The composite oxide according to claim 1, further comprising a carrier, wherein a weight ratio of the composite oxide to the carrier is 0.01-1:1, wherein the carrier is one or more inorganic refractory oxide.

3. The composite oxide according to claim 1, wherein a powder X ray diffraction pattern of the composite oxide in a crystalline form has a peak at a diffraction angle 2 theta of 28.5±0.5°.

4. A process for producing a composite oxide, comprising:
    reacting a Rh source, a Mo source, a V source, an optional Ni source, and an optional Co source under reaction conditions to obtain the composite oxide,
    wherein an amount of the Rh source, an amount of the Mo source, an amount of the V source, an amount of the Ni source and an amount of the Co source are predetermined such that the composite oxide has a composition as represented by the formula $RhR_xMo_yV_zO_{\delta-\alpha}$, wherein R is Ni, Co or a combination of Ni and Co, x=0-3.0, y=0.1-0.9, δ is a positive number at which a valency of oxygen in the composite oxide reaches a balance, α is 0, when R represents the combination of Ni and Co, a molar ratio of Ni:Co is 0.01-20:1,
    optionally a step of partially reducing the composite oxide so that α ranges from more than 0 to δ/2, and
    optionally a step of supporting the composite oxide on a carrier.

5. The process according to claim 4, wherein the Rh source is one or more selected from the group consisting of water soluble inorganic acid salts and water soluble organic acid salts of Rh, and nitrates and acetates of Rh, the Ni source is one or more selected from the group consisting of water soluble inorganic acid salts and water soluble organic acid salts of Ni, and nitrates and acetates of Ni, the Co source is one or more selected from the group consisting of water soluble inorganic acid salts and water soluble organic acid salts of Co, and nitrates and acetates of Co, the Mo source is one or more selected from the group consisting of water soluble inorganic acid salts, water soluble organic acid salts and ammonium oxometallates of Mo, the V source is one or more selected from the group consisting of water soluble inorganic acid salts, water soluble organic acid salts and ammonium oxometallates of V, the optional carrier is one or more selected from the group consisting of $SiO_2$, $Al_2O_3$, $MgO$—$SiO_2$, $MgO$—$Al_2O_3$, $Al_2O_3$—$SiO_2$, $CaO$—$SiO_2$, $CaO$—$MgO$—$SiO_2$ and precursors thereof, and an amount of the carrier is predetermined so that a weight ratio of the composite oxide to the carrier (calculated as the inorganic refractory oxide) is 1-3:1.

6. The process according to claim 4, wherein the Rh source, the Mo source, the V source, the Ni source and the Co source are each in a form of an aqueous solution, further comprising mixing the Rh source, the Mo source, the V source, optionally the Ni source, and optionally the Co source to form a reaction mixture, subjecting the reaction mixture to coprecipitation to form an aqueous slurry, dehydrating, drying and calcinating the aqueous slurry to obtain the composite oxide.

7. The process according to claim 6, wherein the reaction mixture is adjusted to a pH value of 3-10 and maintained a reaction temperature of 60-90 degrees Celsius, for a reaction duration of 1-12 h, wherein the drying step is carried out at a drying temperature of 60-150 degrees Celsius for a drying duration of 4-48 h, wherein the calcination step is carried out at a calcination temperature of 400-900 degrees Celsius for a calcination duration of 3-10 h.

8. The process according to claim 6, wherein the aqueous solution of the Mo source further contains ammonia at a concentration of 1-3 mol/L, and/or the aqueous solution of the V source further contains a $C_{2-6}$ polycarboxylic acid at a concentration of 0.1-0.5 mol/L.

9. A process for coproducing ethanol and acetaldehyde by a methane selective oxidation reaction, comprising obtaining a catalyst of claim 1, contacting methane with the catalyst under a methane selective oxidation reaction condition.

10. The process according to claim 9, wherein the methane selective oxidation reaction condition comprises a reaction temperature of 300-800 degrees Celsius, a reaction pressure of 0.1-5.0 MPa (gage), a feeding gas composition (by molar) of $CH_4:O_2:H_2O=1:0.1-1:0.2-10$, and a methane space velocity of 1200-3500 $h^{-1}$.

11. A process for coproducing ethanol and acetaldehyde by a methane selective oxidation reaction, comprising:
produce a composite oxide according to the process of claim 4,
contacting a feeding gas with the composite oxide at 300-800 degrees Celsius and a pressure of 0.1-5.0 MPa (gage), and
wherein the feeding gas comprises methane, oxygen, and steam at a molar ratio of 1:0.1-1:0.2-10.

12. The composite oxide according to claim 1, wherein $x=0.01-3.0$, $y=0.2-0.7$, $z=0.2-0.9$, $\alpha$ is 0 to $\delta/4$, when R represents the combination of Ni and Co, the molar ratio of Ni:Co is 0.1-10:1.

13. The composite oxide according to claim 1, wherein $x=0.5-2.5$, $y=0.4-0.6$, $z=0.5-0.8$, when R represents the combination of Ni and Co, the molar ratio of Ni:Co is 1-3:1.

14. The composite oxide according to claim 1, wherein $x=1.0-2.0$.

15. The composite oxide according to claim 2, wherein the weight ratio of the composite oxide to the carrier is 0.1-0.3:1, the carrier is one or more selected from the group consisting of $SiO_2$, $Al_2O_3$, $MgO$—$SiO_2$, $MgO$—$Al_2O_3$, $Al_2O_3$—$SiO_2$, $CaO$—$SiO_2$, and $CaO$—$MgO$—$SiO_2$.

16. The composite oxide according to claim 3, wherein the powder X ray diffraction pattern has peaks at diffraction angles 2 theta of 18.5±0.5°, 28.5±0.5°, 31.5±0.5°, and 34.5±0.5°.

17. The process according to claim 9, wherein the suitable methane selective oxidation reaction condition comprises a reaction temperature of 500-600 degrees Celsius, a reaction pressure of 0.5-1.0 MPa (gage), a feeding gas composition (by molar) of $CH_4:O_2:H_2O=1:0.25-0.5:2-4$, and a methane space velocity of 2000-2800 $h^{-1}$.

* * * * *